United States Patent [19]

Fussi

[11] 4,281,108

[45] Jul. 28, 1981

[54] PROCESS FOR OBTAINING LOW MOLECULAR WEIGHT HEPARINS ENDOWED WITH ELEVATED PHARMACOLOGICAL PROPERTIES, AND PRODUCT SO OBTAINED

[75] Inventor: Fernando Fussi, Lesmo, Italy

[73] Assignee: Hepar Industries, Inc., Franklin, Ohio

[21] Appl. No.: 155,674

[22] Filed: Jun. 2, 1980

Related U.S. Application Data

[63] Continuation-in-part of Ser. No. 115,778, Jan. 28, 1980, abandoned.

[51] Int. Cl.$^3$ ............................................. C08B 37/10
[52] U.S. Cl. ...................................... 536/21; 424/183
[58] Field of Search ........................... 536/21; 424/183

[56] References Cited

U.S. PATENT DOCUMENTS 3,247,063  4/1966  Pulver .................................. 424/183

FOREIGN PATENT DOCUMENTS 867064  5/1961  United Kingdom ..................... 536/21
2002406 2/1979  United Kingdom ..................... 536/21

OTHER PUBLICATIONS

Lasker, "Chem. Abst.", vol. 84, 1976, p. 144.869x.

*Primary Examiner*—Johnnie R. Brown
*Attorney, Agent, or Firm*—Cushman, Darby & Cushman

[57] ABSTRACT

The present invention relates to a process for obtaining low molecular weight heparins endowed with pharmacological and therapeutic properties of outstanding interest, starting from normal heparin.

The said process is characterized in that it comprises the following steps:
(a) acidification of normal heparin to obtain heparinic acid,
(b) depolymerization of said heparinic acid by heating in autoclave in the presence of peroxides, to obtain a low molecular weight heparamine,
(c) sulphation of said heparamine to obtain the corresponding low molecular weight heparin.

A further object of the invention is the low molecular weight heparins, or LMW heparins, so obtained, and their utilization in the field of therapeutics.

7 Claims, No Drawings

PROCESS FOR OBTAINING LOW MOLECULAR WEIGHT HEPARINS ENDOWED WITH ELEVATED PHARMACOLOGICAL PROPERTIES, AND PRODUCT SO OBTAINED

This is a Continuation-in-part application of my U.S. Ser. No. 115,778 filed on Jan. 28, 1980, now abandoned.

The subject matter of the present invention is a process for obtaining low molecular weight heparins endowed with pharmacological and therapeutic properties of outstanding interest, starting from normal heparin.

Heparin is a well-known and stable uni- or bivalent salt of the unstable heparinic acid. It is a polymer of a disaccharide unit formed by hexuronic (D-glucuronic and L-iduronic) acids and glucosamine 60- and N-sulphate linked by alpha 1-4 glycoside linkages.

Its anti-clotting properties have been known for many years, since its discovery and isolation from tissues in 1917.

Heparin is present in different forms in many tissues and cells, more or less loosely bound to a protein moiety. In the skin and, partially, in the lungs of different species heparin is present in a high molecular form, which is sensitive to the action of ascorbic acid or of some enzymes thought to be present in the intestinal mucosa. After treatment with ascorbic acid or with intestinal mucosa homogenates, these macromolecular forms of lung or skin heparin can be reduced to the same molecular size as the heparin that can be isolated from the intestinal mucosa.

The heparin isolated from intestinal mucosa having a mean molecular weight ($\overline{MW}$) of 15,000 Dalton, or heparins from other sources reduced to this $\overline{MW}$ by some of the conventional methods as above described, represent the minimal size of the natural molecules of heparin. According to the present invention, such type of heparin is defined as normal heparin. In fact, there exist no enzymes in the body that can further split the heparin from the intestinal mucosa into lower molecular weight fractions, nor have any chemical methods so far been developed able to depolymerize the normal heparin molecule without total loss of its biological activity.

Only certain microbial enzymes, e.g. Heparinase from *Flavobacterium heparinum* are able wholly to dissociate the heparin molecule into modified disaccharide units. This method has been applied in structural studies but has proved unsuitable for obtaining any new biologically active molecules.

One purpose of the present invention is therefore to provide a process such as makes it possible, starting from normal heparin, to obtain lower molecular weight heparin fractions endowed with elevated pharmacological activity.

To achieve the said purpose the present invention proposes a process characterized in that it comprises the following steps:

(a) acidification of normal heparin to obtain heparinic acid, (b) depolymerization of said heparinic acid by heating in an autoclave in the presence of peroxides, to obtain a low molecular weight heparamine, (c) sulphation of said heparamine, to obtain the corresponding low molecular weight heparin.

A scheme of reaction according to the process proposed by the present invention is described below.

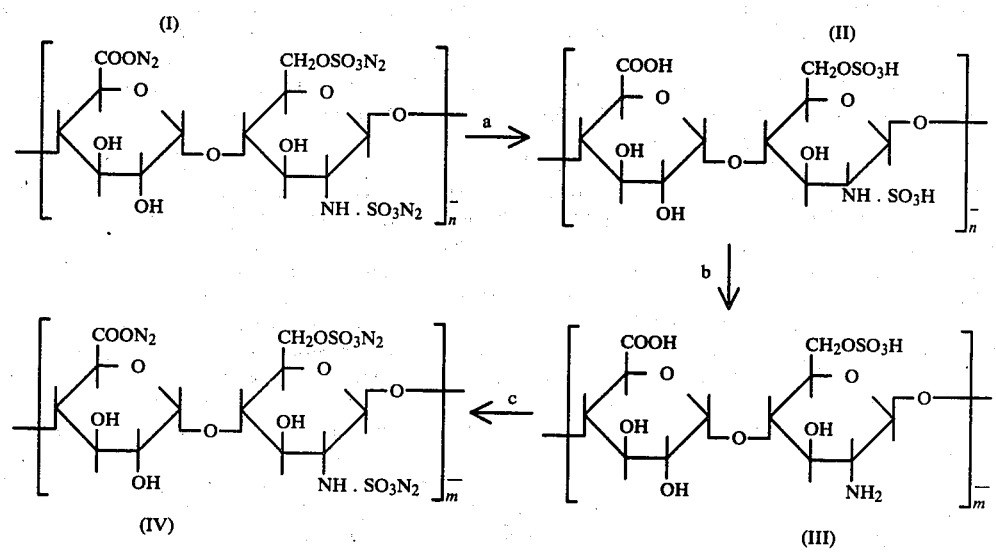

wherein $\overline{m} < \overline{n}$, and $7 < \overline{m} < 22$ when $\overline{n} \approx 26.7$, which is the $\overline{n}$ value corresponding to heparin of $\overline{MW} \approx 15,000$ D.

It is calculated as follows:

$$\overline{n} = \frac{15,000}{562} \approx 26.7$$

wherein 562 is the $\overline{MW}$ of the disaccharide unit (of chemical formula $C_{12}H_{15}O_{16}NS_2Na_3$) represented by the formulas (I) and (IV), reported above.

According to the above scheme of reaction, the formula I indicates the sodium salt of normal heparin; for the sake of simplicity, said formula shows only D-glucuronic acid and not the part of the molecule which contains L-iduronic acid. Similarly, any other univalent or divalent cation, can be present in place of the sodium cation.

The said heparin I is acidified to obtain its free acid, the heparinic acid of formula II, according to the step a shown previously.

The heparinic acid of formula II is depolymerized in the step b, with loss of the majority of the N-sulphate groups and with formation of a heparamine of formula III.

Finally, the heparamine of formula III is treated according to step c by reconstitution of the N-sulphate groups, to obtain the final product according to the invention, i.e. the heparins of formula IV, which are defined as LMW (low Molecular Weight) heparins or RD (Reconstituted Depolymerized) heparins.

According to a more specific description of the process of the invention the said heparinic acid is obtained from normal heparin I by simple acidification or, preferably, by treatment with cationic exchange resins.

The heparinic acid II then goes through the step b of depolymerization, which is carried out in an autoclave in the presence of a peroxide, for example $H_2O_2$, by heating at a pressure preferably between 1 and 2 atm.; the auto-claving can be stopped at preselected times (for instance at 15, 30, 60, 120, 240 minutes). In this way it is possible to obtain final products, i.e. LMW or RD.Heparins, with different mean molecular weights ($\overline{MW}$) in a range approximately between 12,000 and 4,000 D, starting from normal heparin of $\overline{MW}$=15,000 D. The yields of said depolymerization are the same (about 65% by weight) in all instances. The decrease in $\overline{MW}$ is followed by titration of the end reducing groups (Somogji's method) or by decrease of the specific viscosity.

The products of said depolymerization are low molecular weight heparamines III, the molecular weight of which is lower than that of the corresponding starting heparin I down to about one third, according to the preselected different times of autoclaving.

Since in said depolymerization step, and as has been previously stated, the majority of the sulphate groups bound to the nitrogen are lost, the heparamine III is finally—after cooling of the reaction mixture and raising of the pH—subjected to reconstitution of the active sulphuric groups to obtain the final product IV according to the said step c by known methods, such as for example by reaction with sulphotrioxides of nitrogen-containing bases (e.g. pyridine sulphotrioxide, trimethylamine sulphotrioxide; etc.) in the presence of alkaline carbonates, or by reaction with chlorosulphonic acid and nitrogen-containing bases.

The yields of the final products, no matter of the time of autoclaving, are in all cases the same, in terms of weight, as referred to the starting amount of heparin.

For a better comprehension of the invention, some examples of actuation thereof are reported, which are not, however, to be considered limiting.

EXAMPLE 1

A quantity of 20 g of sodium or calcium heparin (anticlotting activity=150 IU/mg) was dissolved in 100 ml of deionized water and placed into a column containing 100 ml of Amberlite ® IRC 120 in H+ FORM.

The column was washed with 100 ml of deionized water and the liquids were collected. The pH of the solution was 1-1.5. 20 ml of a saturated solution of hydrogen peroxide (36% were added and the liquid was heated in an autoclave for 15 minutes at 1 atm. After cooling to room temperature, the pH was raised to 7.2 with 2N NaOH; 16 ml of pyridine and 16 g of pyridine sulphotrioxide were added under stirring.

The reaction lasted for 12 hours, with small addition of pyridine to maintain the pH between 5 and 6. The pH was then raised to 8 with NaOH and the solution was concentrated in vacuo to 100 ml to remove the excess of pyridine. Salts were removed in a mixed-bed ion exchange column and the solution was sterile-filtered and freeze-dried.

Yield: 65% as a white powder with an anti-clotting activity of 85–100 IU/mg and a $\overline{MW}$ (Somogji method) which was ⅔ of the original.

EXAMPLE 2

20 g of sodium or calcium heparin, 150 IU/mg, were dissolved in 100 ml of water for injection and decationized on a cation exchange resin in H+ form.

To the solution (pH=1-1.5) addition was made of 20 ml of peracetic acid (40% solution) and the whole was then autoclaved for 60 minutes at 1 atm.

After cooling and raising the pH to 7.2, 20 g of trimethylamine sulphotrioxide+20 g of $Na_2CO_3$ were added. The reaction mixture was stirred for many hours at a temperature not exceeding 60° C., then passed through a Dowex Retardion ® 11 A 8 column. The pH of the solution was adjusted to 6, the solution was cooled and 3 volumes of ethanol were added. The white precipitate was collected, washed with ethanol or methanol or acetone and dried in vacuo.

The final product possesses an anti-clotting activity of 35–50 IU/mg and a $\overline{MW}$ (Somogji method) which is ⅓ of the original.

EXAMPLE 3

By operating as specified in EXAMPLE 1, but with the following operative conditions: autoclaving for 30 minutes at 2 atm., a final product is obtained with an anti-clotting activity of 35–50 IU/mg and a $\overline{MW}$ which is about ⅓ of the original.

It is firstly stated that the product IV has a chemical composition (content of sulphates, hexosamines, hexuronic acids) and certain physico-chemical properties (specific optical rotation) which are identical to those of the purified heparin I, but gives a different value in the titration of the end reducing groups (Somogji method), a different electrophoretic-mobility and shifted wavelength absorption maxima in the complexes formed with basic dyes, e.g. with toluidine blue.

The LMW heparins (RD heparin) obtained according to the invention show very interesting pharmacological and therapeutic properties as compared with normal heparin I. The most important of these is a modified ratio, either in vitro or in vivo (in experimental animals and in humans), between the anti-thrombotic and the total anti-clotting activities, as measured by the ratio $$\frac{\text{Anti-}X_a \text{ test}}{APTT}$$

where: Anti-Xa test=Yin's test; APTT=Activated Partial thromboplastin time.

The different RD heparins show increasing values of the ratio $$\frac{\text{anti-thrombotic activity}}{\text{total anti-clotting activity}}$$

with decreasing $\overline{MW}$ although the specific anti-clotting activity decreases with decreasing $\overline{MW}$.

In any case, normal heparin with $\overline{MW}$=15,000, has a total anti-clotting activity ≧ 150 IU/mg and a ratio anti-Xa/APTT=1, while RD heparins of the invention have a total anti-clotting activity < 150 IU/mg and an Anti-Xa/APTT>1. In particular, the ratio is almost double for compound IV as compared with compound I. This means that, on the basis of the same anti-clotting activity, the anti-thrombotic activity of compound IV is twice that of normal heparin I; in other words, in terms of anti-clotting activity, half a dose of compound IV, or even less, is required to produce the same anti-thrombotic action as is produced with a whole dose of normal heparin.

These data have been confirmed in experimental animals by measuring the protective action of intravenously administered compounds I and IV against the formation of thrombin and thromboplastin-induced thrombi.

Therefore, in the family of RD Heparins that can be obtained with the present method, it is possible to choose the most suitable product, in terms of specific anti-clotting activity and $$\frac{\text{anti-thrombotic}}{\text{anti-clotting}}$$

ratio, for peculiar uses in the field of the protection against thrombosis.

For instance: a patient in thrombogenic state, with very shortened clotting time, could require an anti-thrombotic agent with a fairly high anti-clotting activity, whereas a patient to be submitted to a surgical intervention, where both the risks of hemorrhage and postoperative thrombosis exist, could require an anti-thrombotic agent with low anti-clotting activity.

Additionally, after subcutaneous administration in humans, compounds IV remain in the bloodstream longer than compound I. Different tests, namely recalcification time, activated partial thromboplastin time (APTT), thrombin time, Anti-Xa activity, were used to check how long compounds IV remains in the circulation.

Moreover, compound IV shows some oral absorption in certain animal species (rats, mice, dogs), whereas compound I is not orally absorbed.

What is claimed is:

1. A process for obtaining low molecular weight heparins endowed with elevated pharmacological properties, comprising the following steps:
    (a) acidification of normal heparin to obtain heparinic acid,
    (b) depolymerization of said heparinic acid by heating in the presence of peroxides, to obtain a low molecular weight heparamine of molecular weight approximately 4000 D to 12,000 D,
    (c) sulphation of said heparamine to obtain the corresponding low molecular weight heparin.

2. A process according to claim 1, wherein said depolymerization takes place in an autoclave.

3. A process according to claim 1, wherein said sulphation takes place by treatment with sulphotrioxides of nitrogen-containing organic bases, in the presence of a base.

4. A process according to claim 3, wherein said base is the free nitrogen-containing bases corresponding to the said sulphotrioxide.

5. A process according to claim 3, wherein said base is an alkaline carbonate.

6. A process according to claim 1, wherein said sulphation takes place by treatment with chloro-sulphonic acid and nitrogen-containing organic bases.

7. A process according to claim 1 wherein the acidification is with a cation exchange resin.

* * * * *